(12) United States Patent
Skelton et al.

(10) Patent No.: US 9,737,719 B2
(45) Date of Patent: Aug. 22, 2017

(54) ADJUSTMENT OF THERAPY BASED ON ACCELERATION

(75) Inventors: Dennis M. Skelton, Woodinville, WA (US); Christopher Poletto, North Oaks, MN (US); Eric J. Panken, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 273 days.

(21) Appl. No.: 13/457,104

(22) Filed: Apr. 26, 2012

(65) Prior Publication Data

US 2013/0289652 A1    Oct. 31, 2013

(51) Int. Cl.
| | | |
|---|---|---|
| *A61N 1/36* | (2006.01) | |
| *A61N 1/365* | (2006.01) | |
| *A61B 5/11* | (2006.01) | |
| *A61B 5/01* | (2006.01) | |
| *A61B 5/021* | (2006.01) | |

(Continued)

(52) U.S. Cl.
CPC ..... *A61N 1/36535* (2013.01); *A61N 1/36139* (2013.01); *A61N 1/36542* (2013.01); *A61B 5/01* (2013.01); *A61B 5/021* (2013.01); *A61B 5/024* (2013.01); *A61B 5/0402* (2013.01); *A61B 5/0476* (2013.01); *A61B 5/0488* (2013.01); *A61B 5/0816* (2013.01); *A61B 5/1116* (2013.01); *A61B 5/1118* (2013.01); *A61B 2562/0219* (2013.01); *A61N 1/36071* (2013.01); *A61N 1/36146* (2013.01); *A61N 1/36153* (2013.01); *A61N 1/36171* (2013.01); *A61N 1/36175* (2013.01); *A61N 1/36185* (2013.01)

(58) Field of Classification Search
CPC ............ A61N 1/36535; A61N 1/36542; A61N 1/36139; A61B 5/11; A61B 5/1116; A61B 5/1118; A61B 5/686; A61B 5/7264
USPC ....................................... 607/2, 6, 18, 19, 62
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Edward Moran
*Assistant Examiner* — Pamela M Bays
(74) *Attorney, Agent, or Firm* — Shumaker & Sieffert, P.A.

(57) ABSTRACT

A medical device provides stimulation therapy to a patient based on a set of therapy parameters. One or more therapy parameters may be automatically adjusted based on acceleration forces detected by a sensor, the acceleration forces being applied to the patient. In some examples, adjustments to one or more therapy parameter may be made based on an algorithm. The algorithm may be defined by acceleration and therapy parameter value pairs associated with opposite patient positions.

35 Claims, 8 Drawing Sheets

(51) Int. Cl.
*A61B 5/024* (2006.01)
*A61B 5/0402* (2006.01)
*A61B 5/0476* (2006.01)
*A61B 5/0488* (2006.01)
*A61B 5/08* (2006.01)

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,330,510 A * | 7/1994 | Legay ............... A61N 1/36542 607/19 |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A * | 1/1997 | Sheldon ............ A61N 1/36542 607/19 |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |

(56) References Cited

U.S. PATENT DOCUMENTS

| | | |
|---|---|---|
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1* | 12/2006 | Koh .................. A61N 1/36542 607/19 |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol et al. |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 7,822,481 B2 | 10/2010 | Gerber et al. |
| 7,853,322 B2 | 12/2010 | Bourget et al. |
| 7,957,797 B2 | 6/2011 | Bourget et al. |
| 7,957,809 B2 | 6/2011 | Bourget et al. |
| 8,032,229 B2 | 10/2011 | Gerber et al. |
| 8,126,567 B2 | 2/2012 | Gerber et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1* | 5/2007 | Wang .................. A61B 5/1116 345/419 |

(56) References Cited

U.S. PATENT DOCUMENTS

| | | |
|---|---|---|
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1* | 1/2010 | Panken ......................... 600/587 |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1* | 1/2010 | Panken et al. .................. 607/62 |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |
| 2011/0270134 A1 | 11/2011 | Skelton |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 p. 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

(56) References Cited

OTHER PUBLICATIONS

Ang et al., "Physical model of a MEMS accelerometer for low-g motion tracking applications," 2004 IEEE International Conference on Robotics and Automation, vol. 2, pp. 1345-1351, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference.On Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, May 1994, 2 pp.
Lau, "Strategies for Generating Prolonged Functional Standing Using Intramuscular Stimulation or Intraspinal Microstimulation," IEEE Transactions on Neural Systems and.Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain interrelate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.

(56) References Cited

OTHER PUBLICATIONS

U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton et al.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,431, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

| Program Table Record | Accelerometer Output | Amplitude (V) | Pulse Width (μs) | Frequency (Hz) | Electrode Configuration |
|---|---|---|---|---|---|
| 1 | [X1, Y1, Z1] | 2.0 | 150 | 10 | 1+ 2- |
| 2 | [X2, Y2, Z2] | 2.5 | 200 | 50 | 1- 2+ |
| 3 | [X3, Y3, Z3] | 1.0 | 100 | 40 | 3- 2+ |
| 4 | [X4, Y4, Z4] | 6.6 | 100 | 40 | 1- 3+ |
| 5 | [X5, Y5, Z5] | 8.3 | 100 | 35 | 8- 6+ |

FIG. 4

ADJUSTMENT OF THERAPY BASED ON ACCELERATION

TECHNICAL FIELD

The disclosure relates to medical devices, and more particularly, medical devices that deliver therapy.

BACKGROUND

A variety of types of medical devices are used for chronic, e.g., long-term, provision of therapy to patients. As examples, electrical stimulation pulse generators are used for chronic delivery of cardiac pacing and/or neurostimulation therapies, and pumps are used for chronic delivery of therapeutic agents, such as drugs. Typically, such devices provide therapy continuously or periodically according to parameters specified by a clinician.

In some cases, a medical device may be deliver therapy according to one of a plurality of stored therapy programs. Selections may be made from among the plurality of programs to accommodate different physiological conditions of the patient. For example, the symptoms, e.g., the intensity of pain, of patients who receive spinal cord stimulation (SCS) therapy may vary over time based on the activity level or posture of the patient, the specific activity undertaken by the patient, or the like. Accordingly, different therapy programs or parameter settings may be delivered at different times, depending on the patient activity level or posture.

SUMMARY

In general, the disclosure is directed to making adjustments to one or more therapy parameters based on detected acceleration. By making changes in therapy parameters based on acceleration, the system of this disclosure may be able to provide adjustments to therapy to compensate for acceleration values greater than 1G. In some examples, a minimal number of acceleration values are associated with one or more therapy parameters during programming. The remaining acceleration values that may be experienced by a patient may have an associated therapy parameter value calculated based on an algorithm created during programming using as few as two separate acceleration therapy parameter value pairs.

In one example, the disclosure is directed to a method comprising receiving data representative of a relationship between a first therapy parameter value for delivery of a therapy while a patient is in a first position, the first therapy parameter value associated with a first acceleration value and a second therapy parameter value for delivery of the therapy while the patient is in a second position, the second therapy parameter value associated with a second acceleration value, wherein the first position is opposite the second position; sensing a third acceleration value; generating a third therapy parameter value for delivery of a therapy to a patient based on the first therapy parameter value and the second therapy parameter value, and a relationship of the third acceleration value to the first and second acceleration values; and controlling a medical device to deliver the therapy to the patient based on the third therapy parameter value.

In another example, the disclosure is directed to a system comprising an acceleration sensor configured to detect a first acceleration value while a patient is in a first position, a second acceleration value while the patient is in a second position, and a third acceleration value while the patient is in a third position, the first position opposite the second position; a processor configured to: receive data representative of a relationship between a first therapy parameter value for delivery of a therapy while the patient is in the first position, the first therapy parameter value associated with the first acceleration value and a second therapy parameter value for delivery of therapy while the patient is in the second position, the second therapy parameter value associated with the second acceleration value, and generate a third therapy parameter value for delivery of a therapy to the patient based on the first therapy parameter value and the second therapy parameter value, and a relationship of the third acceleration value to the first and second acceleration values; and a therapy deliver module configured to deliver the therapy to the patient based on the third parameter value.

In another example, the disclosure is directed to a computer-readable medium containing instructions. The instructions cause a programmable processor to receive a first acceleration value from at least one sensor while a patient is in a first position; generate a first therapy parameter value while the patient is in the first position; associate the first therapy parameter value with the first acceleration value; receive a second acceleration value from the sensor while the patient is in a second position, the first position opposite the second position; generate a second therapy parameter while the patient is in the second position; associate the second parameter value with the second acceleration value; define an algorithm based on the association between the first acceleration value and the first therapy parameter value and the association between the second acceleration value and the second therapy parameter value; receive a third acceleration value; and generate a third therapy parameter value based on inputting the third acceleration value into the algorithm.

In another example, the disclosure is directed to a system comprising means for receiving a first acceleration value from at least one sensor while a patient is in a first position; means for generating a first therapy parameter value while the patient is in the first position; means for associating the first therapy parameter value with the first acceleration value; means for receiving a second acceleration value from the sensor while the patient is in a second position, the first position opposite the second position; means for generating a second therapy parameter while the patient is in the second position; means for associating the second parameter value with the second acceleration value; means for defining an algorithm based on the association between the first acceleration value and the first therapy parameter value and the association between the second acceleration value and the second therapy parameter value; means for receiving a third acceleration value; and means for generating a third therapy parameter value based on inputting the third acceleration value into the algorithm.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 4 illustrates an example patient parameter value table that may be used for closed-loop adjustment of therapy.

DETAILED DESCRIPTION

Figure 1:
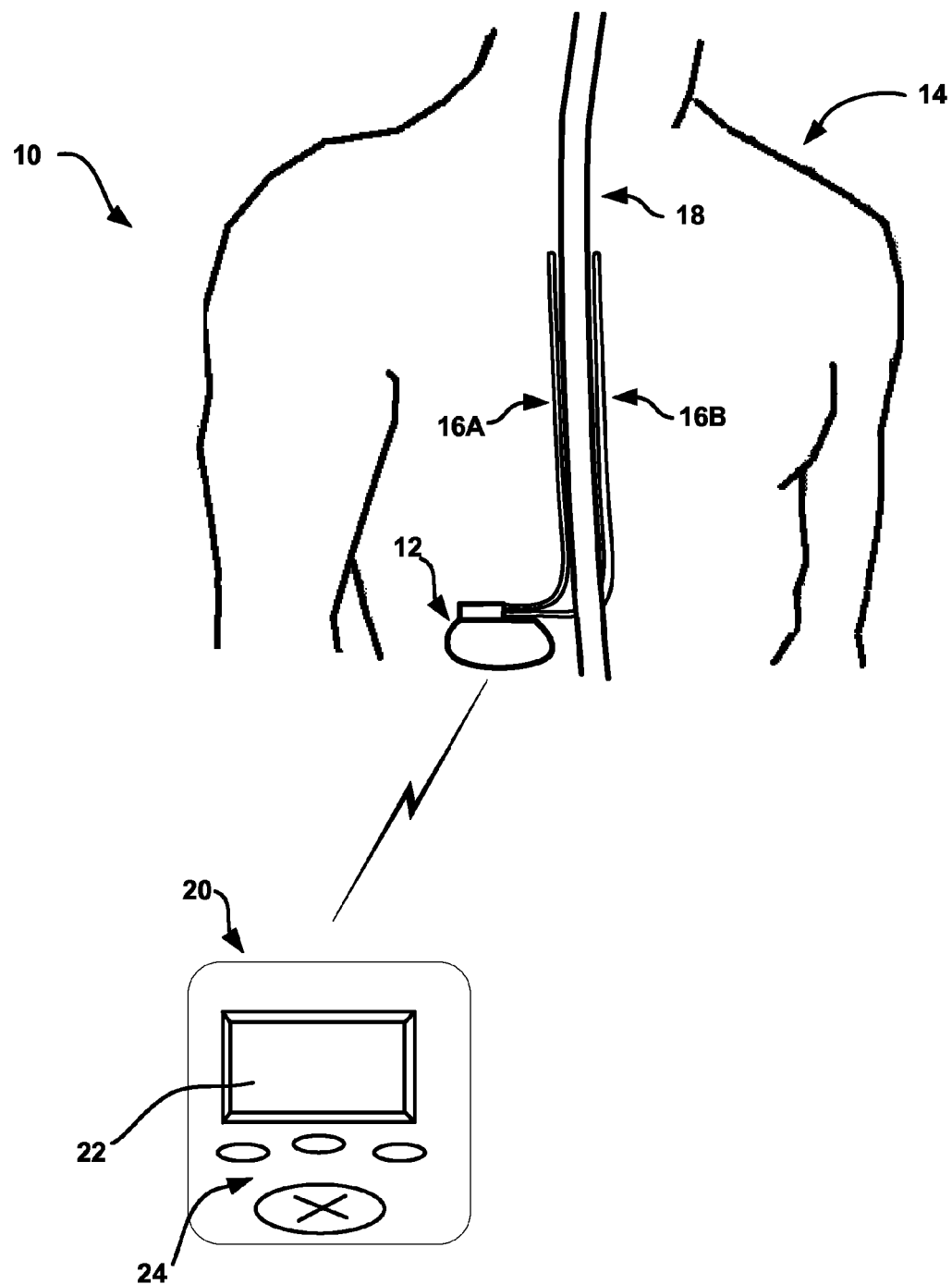
FIG. 1 is conceptual diagram illustrating an example system that facilitates closed-loop therapy adjustment according to an example the present disclosure.

The present disclosure is directed to providing therapy adjustments based on acceleration forces exerted on a patient. In some examples, the force felt by the patient may be due to the gravitational field of the Earth and the acceleration may be equal to the gravitational constant G (9.8 m/s$^2$). Because the gravitational field has a particular orientation, a patient's movements and positions may change how gravity affects a particular portion of the body or object within the body of the patient. For example, a patient's spinal cord may move relative to the patient's spinal column in response to the gravitational field. The spinal cord may, for example, be closer to the spinal column when a patient is lying on their back than when sitting up, e.g., due to compression of tissue. In another example, electrodes implanted within a patient may move relative to a particular point within the patient's body.

In some examples, additional forces may also be exerted on a patient's body. For example, when a patient is riding in a car or an airplane, an additional acceleration force from the movement of the car or airplane may be exerted on the patient. This additional force may also cause the spinal cord, for example, to move within the patient. In some examples, this additional force may result in a force felt by the patient greater than ±1G. Notably, in a car or airplane, or other moving vehicle, this additional force may occur without regard to the posture in which the patient resides.

In some examples, a relative location change between an electrode providing stimulation and the target of the stimulation may result in less effective stimulation therapy. The change in relative location may be a result of movement by the target tissue, the electrode, or a combination of both. In some examples, output from a sensor that detects acceleration may be used in order to determine an appropriate modification to the stimulation therapy provided to the patient. For example, in addition or as an alternative to mapping the sensor output to a patient posture, the sensor output may be used more directly to determine an appropriate modification or modifications to the stimulation therapy provided to the patient. In some examples, a particular patient position may correlate to more than one acceleration value depending on the patient's circumstances. Similarly, the same acceleration value may correspond to different positions. However, by using the detected acceleration value, therapy parameters may be adjusted to compensate for movement of the patient's spinal cord within the spinal column, regardless of patient position.

In some examples, a patient therapy system may be implanted within a patient in order to treat one or more symptoms, such as pain. After implantation, the system may be calibrated in order to determine the appropriate therapy parameters for treatment of the patient's symptoms. Calibration may be performed, for example, by adjusting one or more therapy parameters based on patient feedback. In particular, a patient may select different therapy parameter values for different positions or postures in which the patient resides. For example, the patient may select therapy parameter values that are perceived by the patient as efficacious in addressing symptoms when the patient occupies particular postures. The results of the calibration may be used to define an algorithm that may be used to automatically adjust a therapy parameter value based on a current acceleration reading. In general, the algorithm may be used to either adjust a particular therapy parameter value, or to make adjustments to more than one therapy parameter within a therapy program.

In some examples, calibration may be performed while the patient is in a particular position or posture, such as sitting. In some examples, calibration may be performed while the patient is in more than one position or posture, or while different acceleration forces are applied to the patient. For example, calibration may occur while a patient is sitting or standing upright, while a patient is upside down, lying in a prone position, lying in a supine position, lying on their left side or lying on their right side. In some examples, calibration may occur in at least one pair of opposing positions. The opposing position pairs may include, for examples, lying in a supine position and lying in a prone position, lying on their left side and lying on their right side, and standing upright and being upside down. While the patient is in each position, the acceleration forces felt by the patient may be recorded in addition to the calibrated therapy parameters. The acceleration forces in combination with the calibrated therapy parameters may be used to define one or more equations to be used to determine the appropriate therapy parameters while different acceleration forces are felt by the patient. For example, the voltage or current amplitude of stimulation associated with appropriate treatment while the patient was in two different positions may be used to define a linear equation that may be used to determine an appropriate voltage or current amplitude for therapy delivery under opposite acceleration forces. For example, a patient may lay first on their right side and then on their left side during calibration. The acceleration and therapy parameter values from each position may be used to define the algorithm used to determine an appropriate voltage or current amplitude based on a current acceleration value. In some examples, a linear equation may be used to determine appropriate therapy parameter values outside of the ones used to define the linear equation. For example, appropriate therapy parameters may be determined under acceleration forces greater than ±(plus or minus) 1G. In some examples, a nonlinear equation may be used to define the relationship between detected acceleration force and a particular therapy parameter.

In various examples, acceleration may be detected in one, two or three dimensions. For example, a single axis accelerometer may be used to sense acceleration along a chosen axis. In other examples, three single axis accelerometers or a tri-axis accelerometer may be used to detect acceleration forces in three dimensions. In still other examples, two single axis accelerometers or a dual-axis accelerometer may be used.

In some examples where a single axis accelerometer is used, the orientation of the accelerometer may be made on a patient by patient basis. For example, during calibration of an implantable therapy device, a determination may be made regarding which axis of the body results in the greatest changes in therapy parameters in response to changes in acceleration. This may be important because a single axis accelerometer lacks resolution for changes in acceleration along the other axes. The selection of the appropriate alignment of the single axis accelerometer may be made based on which axis has the most change in therapy parameters based on change in acceleration. For example, an axis perpendicular to the spine may be selected. For a particular patient, the spinal cord may have greater movement in response to changes in acceleration along the lateral-medial axis or the anterior-posterior axis. In another examples, the axis may be chosen by which axis correlates to therapy parameters that are least affected by changes in acceleration along the other two axes. In some examples, each axis is checked to determine which axis is most sensitive to spinal cord movement. In some examples, the axis of the implantable therapy device may not align with the axis of interest.

In some examples, a direction may be selected for determination of acceleration values by the sensor. For example, acceleration values may only be used from a single axis of a multi axis accelerometer, or one of multiple single axis accelerometers may be selected for use. The selection may be based on the effect of spinal cord movement in a second and a third direction on therapy parameter values, where the second and third directions are perpendicular to the selected direction. This allows for the most sensitive axis to be selected and for changes in a therapy parameter value to be based on an acceleration value along a single axis, regardless of the type of acceleration sensor used.

FIG. 1 is a conceptual diagram illustrating an example system 10 that facilitates closed-loop therapy adjustment according to the disclosure. In the illustrated example, system 10 includes an IMD 12, which is implanted within a patient 14, and delivers electrical stimulation therapy to patient 14. In various examples, IMD 12 takes the form of an implantable electrical stimulation generator, and delivers electrical stimulation therapy to patient 14 in the form of a programmable stimulation signal (e.g., in the form of electrical pulses or substantially continuous-time signals).

IMD 12 delivers electrical stimulation therapy to patient 14 via leads 16A and 16B (collectively "leads 16"), and more particularly, via one or more stimulation electrodes carried by leads 16, e.g., in any of a variety of unipolar, bipolar or multipolar arrangements. Leads 16 may also carry one or more sensing electrodes. Leads 16 may, as shown in FIG. 1, be implanted proximate to the spinal cord 18 of patient 14, and IMD 12 may deliver spinal cord stimulation (SCS) therapy to patient 14 in order to, for example, reduce pain experienced by patient 14. Because a patient's spinal cord floats within the spinal canal, the distance between a particular electrode of lead 16 and the spinal cord may change based on the effects of gravity or other acceleration forces. However, the disclosure is not limited to the configuration of leads 16 shown in FIG. 1 or the delivery of SCS therapy. For example, one or more leads 16 may extend from IMD 12 to the brain (not shown) of patient 14, and IMD 12 may deliver deep brain stimulation (DBS) therapy to patient 14 to, for example, treat tremor, Parkinson's disease, epilepsy or other movement disorders or other neurological disorders. As further examples, one or more leads 16 may be implanted proximate to the pelvic nerves (not shown), stomach (not shown), or sexual organs (not shown), or associated nerves, and IMD 12 may deliver electrical stimulation therapy to treat urinary or fecal incontinence, gastroparesis, sexual dysfunction, peripheral neuropathy, post-operative pain mitigation, ilioinguinal nerve stimulation, intercostal nerve stimulation, gastric stimulation for the treatment of gastric mobility disorders and obesity or muscle stimulation (e.g., functional electrical stimulation (FES) of muscles). In various examples, the relative position of a stimulation target and the electrodes providing stimulation may change based on the current effects of gravity or other acceleration forces on the patient.

IMD 12 includes a sensor that is configured to sense at least one patient parameter. The patient parameter may include parameters that may affect the efficacy of therapy or indicate a parameter that affects the efficacy of therapy, e.g., activity, activity level, posture, acceleration, or a physiological parameter of patient 14. Physiological parameters may include heart rate, respiration rate, respiratory volume, core temperature, blood pressure, blood oxygen saturation, partial pressure of oxygen within blood, partial pressure of oxygen within cerebrospinal fluid, muscular activity, arterial blood flow, electromyogram (EMG), an electroencephalogram (EEG), an electrocardiogram (ECG) or galvanic skin response. In other examples, a sensor used to sense such patient parameters may be implanted at a site within patient 14 or worn on the exterior of the patient, in which case the sensor may be coupled to IMD 12. An example sensor is a 3-axis accelerometer located within IMD 12 to sense acceleration along one or more axes. Patient parameter values detected by IMD 12 based on the signals generated by such a sensor may correspond to an activity or posture undertaken by patient 14, a level of acceleration being felt by the patient, or a gross level of physical activity, e.g., activity counts based on footfalls or the like. For example, IMD 12 may associate the signal generated by a 3-axis accelerometer or multiple single-axis accelerometers (or a combination of a three-axis and single-axis accelerometers) with a particular therapy program.

In some examples IMD 12 delivers therapy according to a therapy parameter or therapy program selected from two or more stored therapy parameters or therapy programs, or a therapy parameter or therapy program generated by extrapolating based on two therapy parameters or programs, where the two therapy programs were generated while the patient was in opposite positions. That is, for example, the first therapy program may have been generated while patient 14 was lying on their back and the second therapy program may have been generated while patient 14 was lying on their front. In particular, IMD 12 may select a therapy program or extrapolate parameters based on two stored therapy programs and the value of a sensed patient parameter. Interpolation or extrapolation of therapy parameters may be based on an algorithm that is defined by two stored therapy parameters generated while patient 14 was in opposite positions. Different therapy programs may provide efficacious therapy for different physiological conditions of the patient. For example, the symptoms, e.g., the intensity of pain, of patients who receive spinal cord stimulation (SCS) therapy may vary over time based on the activity level or posture of the patient, the specific activity undertaken by the patient, or the like. In addition, the distance between the electrodes and the intended stimulation site may vary based on the level of acceleration felt by the patient. Accordingly, IMD 12 may select different therapy parameters for therapy delivery at different times, depending on a sensed patient parameter value, which may be, for example, the patient activity level, level of acceleration, or posture of patient 14.

A therapy program may be defined by a set of one or more therapy parameters that define an aspect of the therapy delivered by IMD 12. For example, a program that controls delivery of electrical stimulation by IMD 12 in the form of electrical stimulation pulses may define a voltage or current pulse amplitude, a pulse width, a pulse rate, for stimulation pulses delivered by IMD 12, a cycle of stimulation delivery (e.g., a timing of when IMD 12 is in an on mode or an off/sleep mode), a continuous waveform, and so forth. Further, each of leads 16 includes electrodes (not shown in FIG. 1), and the parameters for a program that controls delivery of stimulation therapy by IMD 12 may include information identifying an electrode combination that designates, which electrodes have been selected for delivery of pulses according to the program, and the polarities of the selected electrodes, i.e., where electrode combination and polarities together define an electrode configuration for the program. In addition, a therapy parameter may include the particular pattern and/or locations of anodes and cathodes of the electrodes of leads 16 (the "electrode combination").

In some examples, IMD 12 stores the therapy programs as a plurality of records that are stored in a table or other data structure that may be continually updated as IMD 12 "learns" associations of therapy information with patient parameter values. Example techniques for generating and updating the records within the table or other data structure are described in commonly-assigned U.S. Patent Application Publication No. 2007/0150026 by Bourget et al., entitled, "CLOSED-LOOP THERAPY ADJUSTMENT" and filed on Dec. 1, 2006, and commonly assigned U.S. Pat. No. 7,769,464 by Gerber et al., entitled "THERAPY ADJUSTMENT" and filed on Apr. 30, 2007 each of which is incorporated herein by reference in its entirety. While the remainder of the disclosure refers primarily to tables, the present disclosure also applies to other types of data structures that store therapy programs and associated physiological parameters.

As described below with reference to FIG. 4, each record within a table stored within IMD 12 may include at least one patient parameter value and associated therapy information. The therapy information may define one or more therapy parameter values, absolute or percentage adjustments for one or more therapy parameters or a complete therapy program that IMD 12 implements to deliver therapy to patient 14. As described in further detail below, when IMD 12 detects a value of a patient parameter, IMD 12 may adjust the therapy delivery based on a stored algorithm or therapy information in the records of the table. For example, upon determining a patient parameter value, such as an acceleration value, IMD 12 may locate a record in the stored table including the patient parameter value and deliver therapy according to the therapy parameter value associated with the patient parameter value. Alternatively, IMD 12 may extrapolate a new therapy parameter value based on an algorithm defined by two therapy parameter values if the table does not include any records that associate the particular patient parameter value with a therapy parameter value.

In the illustrated example, system 10 also includes a programming device 20, which may, as shown in FIG. 1, be a handheld computing device. Programming device 20 allows a user to interact with IMD 12. Programming device 20 may, for example, communicate via wireless communication with IMD 12 using radio-frequency (RF) telemetry techniques, or any other techniques known in the art. Programming device 20 may, as shown in FIG. 1, include a display 22 and a keypad 24 to allow the user to interact with programming device 20. In some examples, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some examples, keypad 24 may include an increase amplitude button and a decrease amplitude button to directly adjust stimulation amplitude.

In some examples, programming device 20 is a patient programmer used by patient 14 to control the delivery of neurostimulation therapy by IMD 12. Patient 14 may use programming device 20 to activate or deactivate, e.g., start or stop, neurostimulation therapy. Patient 14 may also use programming device 20 to adjust the therapy. For example, when IMD 12 is in one mode, a patient may use programming device 20 to manually select one or more programs from among a plurality of stored programs to be the current programs used by IMD 12 to deliver therapy, e.g., patient 14 may switch from one program to another using programming device 20. Further, patient 14 may also use programming device 20 to adjust therapy by adjusting one or more stimulation parameters, e.g., adjust the voltage or current amplitude, pulse width, or pulse rate of delivered stimulation pulse, for the one or more current programs. However, as described herein, in another mode, IMD 12 may be programmed to automatically extrapolate a new program based on a stored algorithm and a sensed patient parameter value.

In some examples, the table of therapy programs and associated patient parameter values may be maintained by and/or stored within programming device 20 instead of IMD 12. Accordingly, one or both of IMD 12 and programming device 20 may provide closed-loop adjustment of the therapy delivered by IMD 12. In examples in which programming device 20 maintains the table, programming device 20 may include sensors that sense the patient parameter, or may receive values of the patient parameter from IMD 12 or another implanted or external sensor. After selecting a program or generating an intermediate program by extrapolating based on the therapy parameters of two therapy programs and a sensed patient parameter value, programming device 20 may send commands to IMD 12 based on therapy information stored in the table to implement closed-loop delivery of therapy.

For ease of description, the provision of closed-loop therapy adjustment will be described hereinafter primarily with reference to examples in which IMD 12 provides the closed-loop therapy adjustments. However, it is understood that both of IMD 12 and programming device 20 are medical devices capable of providing closed-loop therapy adjustments according to the techniques described in the disclosure. Accordingly, in various embodiments, IMD 12 and/or programming device 20 may be configured to control therapy delivered by IMD 12 based on one or more sensed patient parameters.

Figure 2:
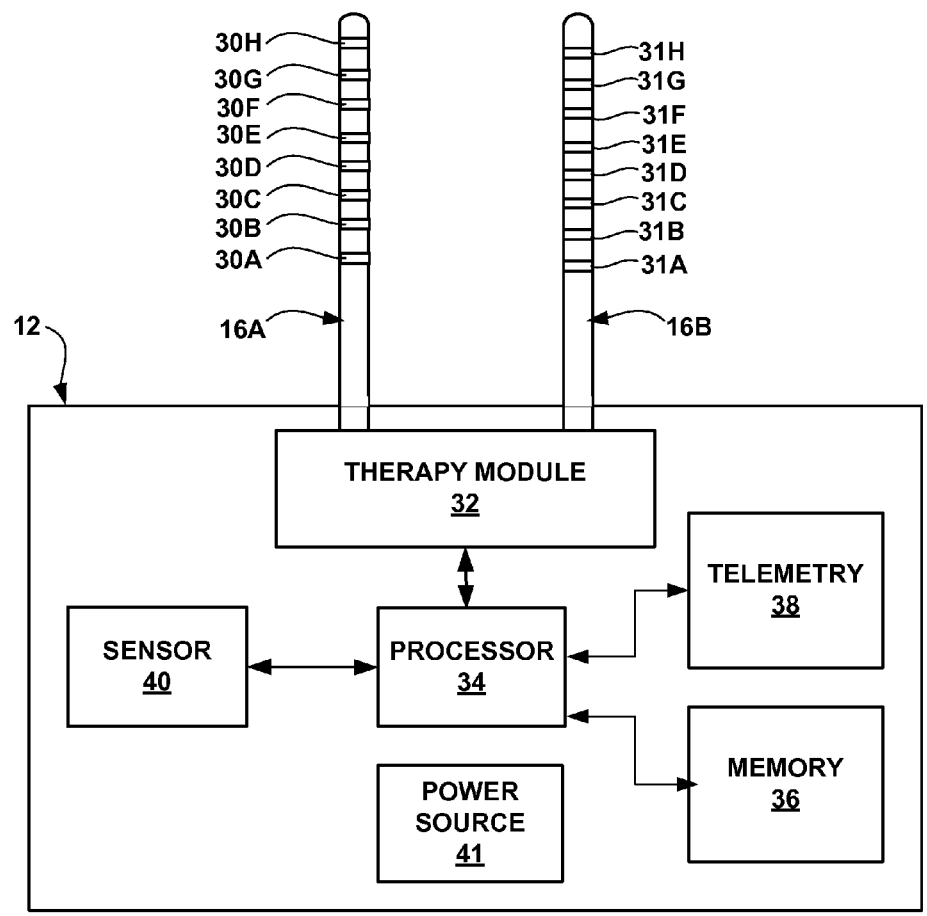
FIG. 2 is a block diagram illustrating an implantable medical device (IMD), as shown in FIG. 1, in greater detail.

FIG. 2 is a block diagram illustrating IMD 12 in greater detail. IMD 12 is coupled to leads 16A, 16B, which include electrodes 30A-H and 31A-H, respectively. IMD 12 may be coupled to leads 16A, 16B either directly or indirectly via a lead extension. IMD 12 includes therapy module 32, processor 34, memory 36, telemetry module 38, sensor 40, and power source 41.

IMD 12 may deliver neurostimulation therapy via electrodes 30A-H of lead 16A and electrodes 31A-H of lead 16B (collectively "electrodes 30 and 31"). In the example shown in FIG. 2, implantable medical leads 16A and 16B are cylindrical. In other examples, leads 16A and 16B may be, at least in part, paddle-shaped (i.e., a "paddle" lead). In some examples, electrodes 30, 31 may be ring electrodes. In other examples, electrodes 30, 31 may be segmented or partial ring electrodes, each of which extends along an arc less than 360 degrees (e.g., 90-120 degrees) around the outer perimeter of the respective lead 16A, 16B. The configuration, type, and number of electrodes 30, 31 illustrated in FIG. 2 are merely exemplary. For example, IMD 12 may be coupled to one lead with eight electrodes on the lead or to three leads with the aid of a bifurcated lead extension.

Electrodes 30, 31 are electrically coupled to a therapy module 32 of IMD 12 via conductors within the respective leads 16A, 16B. Each of electrodes 30, 31 may be coupled to separate conductors so that electrodes 30, 31 may be individually selected, or in some examples, two or more electrodes 30 and/or two or more electrodes 31 may be coupled to a common conductor. In one example, an implantable signal generator or other stimulation circuitry within therapy module 32 delivers electrical signals (e.g., pulses or substantially continuous-time signals, such as sinusoidal signals) to a target tissue site within patient 14 via at least some of electrodes 30, 31 under the control of processor 34. The stimulation energy generated by therapy module 32 may be delivered from therapy module 32 to selected electrodes 30, 31 via a switch matrix and conductors carried by leads 16, as controlled by processor 34.

Processor 34 may include any one or more processors such as a microprocessor, a controller, a digital signal processor (DSP), an application specific integrated circuit (ASIC), a field programmable gate array (FPGA), discrete logic circuitry, or the like. Processor 34 controls the implantable signal generator within therapy module 32 to deliver electrical stimulation therapy according to selected therapy parameters. Specifically, processor 34 controls therapy module 32 to deliver electrical signals with selected voltage or current amplitudes, pulse widths (if applicable), and rates specified by the stimulation parameters (i.e., therapy parameters). The therapy parameters may be defined as part of a therapy program. In addition, processor 34 may also control therapy module 32 to deliver the electrical stimulation signals via selected subsets of electrodes 30, 31 with selected polarities. For example, electrodes 30, 31 may be combined in various bipolar or multi-polar combinations to deliver stimulation energy to selected sites, such as nerve sites adjacent the spinal column, pelvic floor nerve sites or cranial nerve sites. The above-mentioned switch matrix may be controlled by processor 34 to configure electrodes 30, 31 in accordance with a therapy program.

IMD 12 also includes a memory 36, which may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 36 may store program instructions that, when executed by processor 34, cause IMD 12 to perform the functions ascribed to IMD 12 herein. Memory 36 may also store a table of therapy programs or parameters (e.g., the therapy parameters of each therapy program) and associated patient parameter values. In some examples, memory 36 may also store one or more equations or tables for determining one or more therapy parameters based on detected patient parameter values.

In some examples, processor 34 maintains, e.g., creates and modifies, the table stored in memory 36. For example, in some examples, processor 34 maintains the table in accordance with the techniques described in commonly-assigned U.S. Patent Application Publication No. 2007/0150026 by Bourget et al., entitled, "CLOSED-LOOP THERAPY ADJUSTMENT" and filed on Dec. 1, 2006, and commonly assigned U.S. Pat. No. 7,769,464 by Gerber et al., entitled "THERAPY ADJUSTMENT" and filed on Apr. 30, 2007.

IMD 12 includes a sensor 40 that senses one or more patient parameters. Processor 34 detects values of the patient parameter based on the signal generated by sensor 40 as a function of the patient parameter. Sensor 40 may be a sensor that generates an output, such as an electrical signal, based on activity, activity level, acceleration, posture, and/or one or more physiological parameters of patient 14, as discussed above. In some examples, processor 34 receives the electrical signal from sensor 40 and determines a parameter value from the signal. Based on the parameter value, processor 34 may also select or determine a therapy program or therapy parameter adjustment. In some examples, sensor 40 is a 3-axis accelerometer, such as a piezoelectric and/or micro-electro-mechanical accelerometer. In other examples, a single axis accelerometer may be employed for sensor 40, or multiple single axis accelerometers may be used in place of one 3-axis accelerometer.

In some examples, processor 34 processes the analog output of sensor 40 to determine acceleration information. The analog output may be digitized using any suitable analog-to-digital converter to permit digital processing of the output of sensor 40. In some examples, IMD 12 includes one or more sensors oriented along various axes, or sensor 40 comprises a single multi-axis, e.g., three-axis, accelerometer. In such examples, processor 34 may process the signals provided by the one or more sensors 40 to determine velocity of motion information for each axis.

In other examples, IMD 12 may include an ultrasonic transducer on at least one of leads 16A, 16B to detect movement relative to a target tissue site. An example of a technique for detecting relative movement between a target tissue site and at least one of leads 16A, 16B is provided in commonly-assigned U.S. Pat. No. 7,406,351 to Wesselink et al., entitled, "ACTIVITY SENSING FOR STIMULATOR CONTROL," and issued on Jul. 29, 2008. As previously described, the movement of leads 16A, 16B within patient 14 may affect the efficacy of therapy, for example, by changing the intensity of stimulation perceived by patient 14. Accordingly, a position of leads 16A, 16B relative to a target tissue site may represent a patient parameter value that may be associated with a therapy parameter value. Upon detecting lead 16A, 16B movement relative to the target tissue site, a therapy parameter value may be adjusted.

Although illustrated in FIG. 2 as including a single sensor 40, systems according to the disclosure may include any number of sensors 40. In various examples, the one or more sensors 40 are housed within a housing (not shown) of IMD 12. However, the disclosure is not so limited. In some examples, one or more sensors 40 are coupled to IMD 12 via additional leads 16 (not shown). Such sensors may be located anywhere within patient 14. In some examples, IMD 12 may be coupled to multiple accelerometer sensors 40 located at various positions within patient 14 or on the external surface of patient 14, and processor 34 may receive more detailed information about the posture of, and activity undertaken by, patient 14. For example, accelerometer sensors 40 may be located within the torso and at a position within a limb, e.g. a leg, of patient 14.

In some examples, one or more sensors 40 may communicate wirelessly with IMD 12 instead of requiring a lead to communicate with the IMD. For example, sensors 40 located external to patient 14 or implanted separately from IMD 12 may communicate wirelessly with processor 34, either directly or via programming device 20. In some examples, one or more sensors 40 may be included as part of or coupled to programming device 20.

Moreover, the disclosure is not limited to examples where sensors 40 are all accelerometers. In some examples, one or more sensors 40 may take the form of, for example, a thermistor, a pressure transducer, or electrodes to detect thoracic impedance or an electrogram. Such sensors 40 may be appropriately positioned within patient 14, or on an external surface of the patient, to allow processor 34 to measure a physiological parameter of patient 14, such as a skin temperature, an arterial or intracardiac pressure, a respiration rate, a heart rate, or a Q-T interval of patient 14.

Processor 34 may also control therapy module 32 to deliver the electrical stimulation to patient 14 according to a therapy parameter extrapolated based on an algorithm stored in memory 36, as described above. In particular, processor 34 may monitor the patient parameter via sensor 40 and generate a therapy parameter setting, a parameter adjustment or a therapy program that is associated with the sensed patient parameter from the stored algorithm. In some examples, therapy programs or parameters generated based on the stored algorithm may then be associated with a current acceleration value, or other patient parameter, and stored in a table in memory 36. A range of patient parameters may be associated with a single therapy program because patient 14 may find the therapy program effective for multiple patient conditions represented by the range of patient parameters. Hence, different ranges of patient parameters may be associated with respective therapy programs or therapy parameter settings.

In some examples, processor 34 may also control therapy module 32 to deliver the electrical stimulation to patient 14 based on a therapy program including one or more therapy parameters extrapolated from therapy parameters stored in memory 36. In particular, processor 34 may monitor acceleration via sensor 40 and extrapolate at least the voltage or current parameter based on the present level of acceleration and previous therapy program/acceleration relationships stored in memory 36. In some examples, processor 34 may store the newly extrapolated therapy program in memory 36 along with the associated acceleration reading. In some examples, processor 34 may reference a stored table in memory 36 prior to extrapolating a therapy parameter. Because the table may include only a certain number of discrete parameter values associated with discrete programs, processor 34 may select the most closely related program (e.g., the program associated with a parameter value that is the closest to the current patient parameter value out of all the parameter values in the table) and implement an algorithm for extrapolating an appropriate therapy parameter or program based in part on a stored algorithm generated based on at least two therapy parameter values.

Processor 34 may monitor the signal from sensor 40 at regular intervals or substantially continuously in order to determine whether to change the therapy parameter value or program by which therapy module 32 delivers electrical stimulation therapy to patient 14. In this way, signals from sensor 40 are used in a closed-loop therapy program adjustment technique implemented by processor 34. In other examples, a separate processor, rather than processor 34 of IMD 12 may be used to monitor the signal from sensor 40 and select therapy programs for implementation based on the sensed patient parameter or extrapolation based on two therapy programs. IMD 12 may include another processor or the separate processor may be included within a separate medical device (either implanted within patient 14 or carried external to patient 14). The separate processor may provide an input to processor 34 that indicates the sensor output or the input to processor 34 may indicate processor 34 should implement a change in therapy program based on the change in the sensor 40 output. In addition, in some examples, the separate processor may also determine a rate of change between adjusting therapy delivery between two or more therapy programs and/or interpolate between therapy parameters of two or more programs. Use of a processor separate from processor 34, and especially a separate processor in another medical device, may help conserve power source 41 and extend the useful life of IMD 12.

IMD 12 also includes a telemetry circuit 38 that allows processor 34 to communicate with programming device 20. Processor 34 may receive program selections, therapy parameter adjustments, or other therapy adjustments that override the therapy program selected by processor 34, as well as commands to initiate or terminate stimulation, from a user, e.g., patient 14, using programming device 20 via telemetry circuit 38. In some examples, processor 34 may store initial program settings based on information received from programming device 20 via telemetry circuit 38. For example, an initial calibration of one or more therapy programs provided by therapy module 32 may be initiated by programming device 20. In some examples, processor 34 also communicates with a clinician programmer to provide diagnostic information stored in memory 36 to a clinician via telemetry circuit 38. The diagnostic information may be, for example, the patient parameter values detected by sensor 40. The clinician programmer may operate similarly to programmer 20, but the clinician programmer may be more fully featured, e.g., provide greater control of or interaction with IMD 12, than programming device 20. Telemetry circuit 38 may correspond to any telemetry circuit known in the implantable medical device arts.

Therapy module 32 and processor 34 may be coupled to power source 41. Power source 41 may take the form of a small, rechargeable or non-rechargeable battery, or an inductive power interface that transcutaneously receives inductively coupled energy. In the case of a rechargeable battery, power source 41 similarly may include an inductive power interface for transcutaneous transfer of recharge power.

Figure 3:
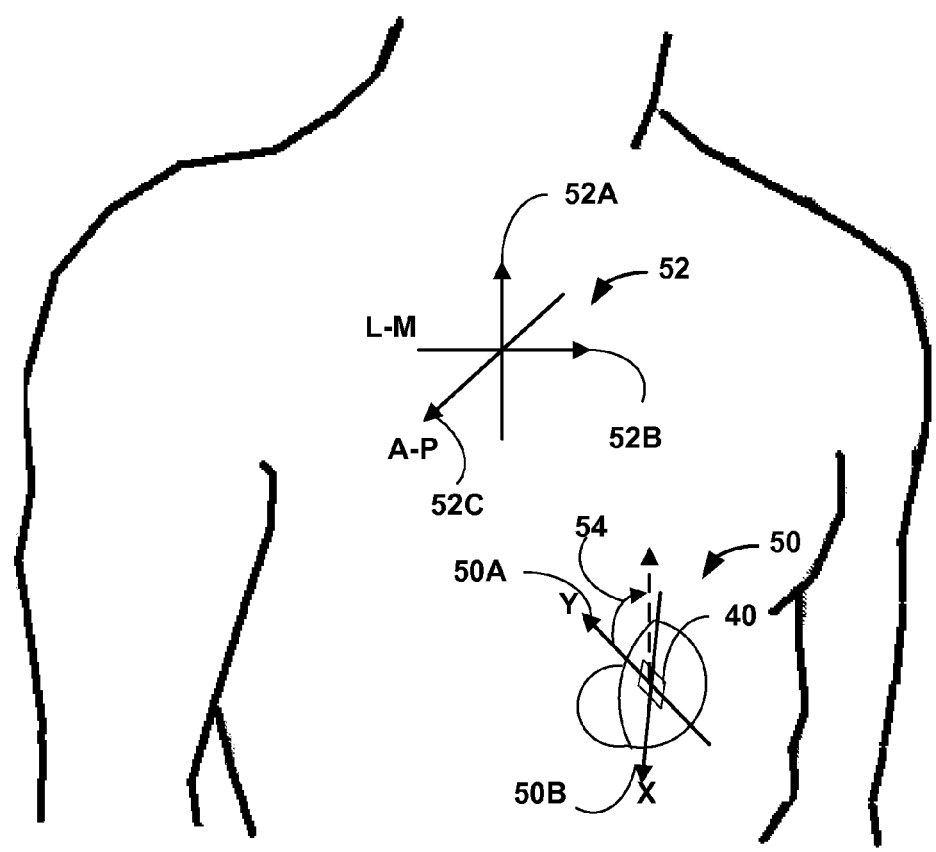
FIG. 3 illustrates the use of an orientation vector to translate sensor signals from a sensor coordinate system to a body coordinate system.

FIG. 3 illustrates the use of an orientation vector to translate sensor signals from a sensor coordinate system into a body coordinate system. In some examples, this may be used when sensor 40 is a single axis accelerometer. IMD 12 is shown implanted within patient 14. As discussed above, sensor 40 may be carried inside a housing of IMD 12. Sensor 40 has a sensor coordinate system 50 that includes y axis 50A and x axis 50B, and a z axis (not shown for simplicity). Patient has a body coordinate system 52 that includes a rostro-caudal (R-C) axis 52A, a lateral/medial (L-M) axis 52B, and anterior/posterior (A-P) axis 52C. This body coordinate system 52 is not necessarily aligned with the sensor coordinate system in FIG. 3. For instance the R-C axis 52A need not align with y axis 50A of the sensor coordinate system, and the L-M axis 52B need not align with the x axis 50B of the sensor coordinate system. IN some embodiments involving misalignment, the output of sensor 40 cannot be used to directly detect the direction of acceleration as felt by the body and defined by the body coordinate system.

In such embodiments, before the output of sensor 40 is used to detect acceleration defined in terms of the body coordinate system, the output of sensor 40 may be corrected for the difference between the two coordinate systems. In some examples, a correction factor is applied to the sensor output. The correction factor may include a roll angle 54.

The roll angle describes the misalignment of the R-C axis 52A and y axis 50A of sensor 40. Similar angles may be used to describe any misalignment between the L-M axis 52 B and the x axis 50B, and any misalignment between the A-P axis 58C and the z axis (not shown) of the sensor 40. Mechanisms for applying correction factors are provided, for example, in commonly-assigned U.S. Pat. No. 6,044, 297, entitled "Posture and Device Orientation and Calibration for Implantable Medical Devices" to Sheldon et al., incorporated herein by reference.

However, the application of the correction factor to a sensor output may be processing intensive. Moreover, the correction factors must be initially determined. In an IMD that will perform an acceleration determination on a regular basis, it may be desirable to eliminate these steps to conserve power.

In some examples, acceleration may be defined in the coordinate system of the sensor rather than in the patient's body coordinate system. In such instances, no correction factor need to be applied to the output of sensor 40 and the correction factors do not need to be derived. In such examples, the process of performing acceleration detection is simplified and saves power and processing time. This may be beneficial in an IMD to conserve limited power supply resources.

To define acceleration in the coordinate system of the sensor, sensor 40 is positioned on, or in, patient 14 in any orientation in a substantially fixed manner. For instance, the sensor may have been implanted in the patient during a surgical procedure, may have been located on the patient using a transcutaneous procedure, may be temporarily or permanently affixed to an external surface of the patient, or may be carried on the patient's clothing or other articles donned by the patient. The orientation of the sensor relative to the patient is substantially unchanging, at least over some period of time during which acceleration detection will occur.

Once the sensor is disposed in relation to the patient's body, the patient is asked to temporarily assume a posture associated with a known acceleration. Outputs from sensor 40 are obtained while the patient is in the assumed posture. In the case of a three-axis accelerometer, these outputs define a vector in three-dimensional space that may, in one example, be expressed in terms of the coordinate system of sensor 40 without regard to the coordinate system of the patient's body. This vector that is defined by the output of the sensor 40 may be any vector in three-dimensional space.

The vector, which may be referred to as a defined acceleration vector, is associated with the known acceleration. This association may occur by storing the defined posture vector or some representative therefore with a designation that identifies the acceleration. Such an association may be stored within a table, data structure, or other organized aggregation of the data in memory 36.

The patient may be asked to assume any number of postures associated with known accelerations in the foregoing manner. As each posture is assumed, and each acceleration value achieved, signals are obtained from sensor 40 that are indicative of a defined acceleration vector that are, in one example, expressed in the coordinate system of sensor 40 without regard to the coordinate system of the patient. The defined acceleration vector or a representation thereof is associated with the posture under definition.

In some examples, one or more of the defined acceleration vectors may be used as an orientation vector, as described in more detail below. The orientation vector may be used to help define a current acceleration and subsequently associate the acceleration reading with a therapy program when the actual acceleration on the patient is unknown. For example, the angle between a defined acceleration vector and a current acceleration vector may be determined.

FIG. 4 illustrates an example patient parameter value table 60 that may be used for closed-loop adjustment of therapy. Table 60 may be stored in memory 36 of IMD 12. As shown in FIG. 4, table 60 includes a plurality of records. In some examples, each record contains a 3-axis accelerometer output, as well as an associated therapy program. In other examples, not shown, table 60 may include a single axis accelerometer output and a single patient parameter, such as current or voltage amplitude. In the example shown in FIG. 4, the therapy parameters of each therapy program are shown in table 60, and include an amplitude, a pulse width, a pulse frequency, and an electrode configuration. Processor 34 may search table 60 based on a currently-detected accelerometer output in order to match therapy to the current condition, e.g., acceleration on the body of patient 14. In some examples, table 60 may only include therapy parameters or programs generated during calibration of IMD 12. For example, the table may include therapy programs or parameters generated while a patient is lying on their back, lying on their right side, lying on their left side, and lying on their front. For acceleration values that do not align with one of the acceleration values recorded during calibration, a corresponding therapy parameter value may be generated based on an algorithm that is defined by at least two of the initial therapy parameter/acceleration value associations stored in table 60. In some examples, the result of the algorithm may be subsequently stored in table 60.

Sensor 40 (FIG. 2) of IMD 12 may include the 3-axis accelerometer, whose output may indicate a relative position of the patient's spinal cord to the spinal cord's initial position. A measured acceleration in each direction creates an acceleration vector. Therefore, each accelerometer output includes an X variable, a Y variable, and a Z variable. The value of the accelerometer may be a raw value or a calibrated value equal either to the acceleration as projected onto an orientation vector, or equal the actual acceleration.

With respect to the therapy information, the amplitude may be in either volts or amps, the pulse width is in microseconds (µs), the pulse frequency is in Hertz (Hz), and the electrode configuration determines the electrodes and polarity used for delivery of stimulation according to the record. With respect to the electrode configuration, the electrodes of leads 16A and 16B may each be assigned a number 1-8. The electrode configuration shown in table 60 indicates which electrode from each lead is being used and whether it has a positive or negative polarity. The amplitude of program table 60 is the voltage amplitude, but other examples may use a current amplitude. In the illustrated example, each record includes a complete set of therapy parameters, e.g., a complete program, as therapy information. In other examples, each record may include one or more individual parameter values, or information characterizing an adjustment to one or more parameter values. In some examples, the parameter values may be learned or generated during the calibration process based on patient feedback when a particular acceleration value is observed. In some examples, a patient may be able to provide adjustments to therapy parameters to ensure efficacious treatment. Patient adjustments may be stored in table 60, and in some examples, an indication that adjustment has occurred may also be stored.

When processor 34 detects an output from the accelerometer, e.g., a particular acceleration vector, processor 34 may automatically deliver therapy appropriate for the patient under the particular acceleration vector by generating a therapy parameter based on an algorithm stored in memory 36 or by selecting a therapy parameter in the table 60 that is associated with an accelerometer output that substantially matches or is within a predetermined range of the detected accelerometer output. The predetermined range may be determined by the clinician or another user, and in some examples, may be customized to patient 14. By providing therapy adjustments automatically, IMD 12 provides closed-loop control of the therapy parameters, which may allow patient 14 to avoid having to manually adjust the therapy each time a particular patient parameter value occurs, e.g., each time the patient engages in a particular activity, activity level or posture. Such manual adjustment of stimulation parameters can be tedious, requiring patient 14 to, for example, depress one or more keys of keypad 24 of programming device 20 (FIG. 1) multiple times during the patient activity to maintain adequate symptom control.

The look-up table 60, however, may be limited in breadth of coverage for all accelerometer outputs because, for example, of limits in the capacity of memory 36. Thus, in some cases, processor 34 may detect an output from the accelerometer that is not present in table 60 or within a predetermined range of an accelerometer output that is present in table 60. In such cases, processor 34 may extrapolate based on an algorithm defined by two programs in table 60 to generate a therapy program that best-suits the detected accelerometer output.

Figure 5:
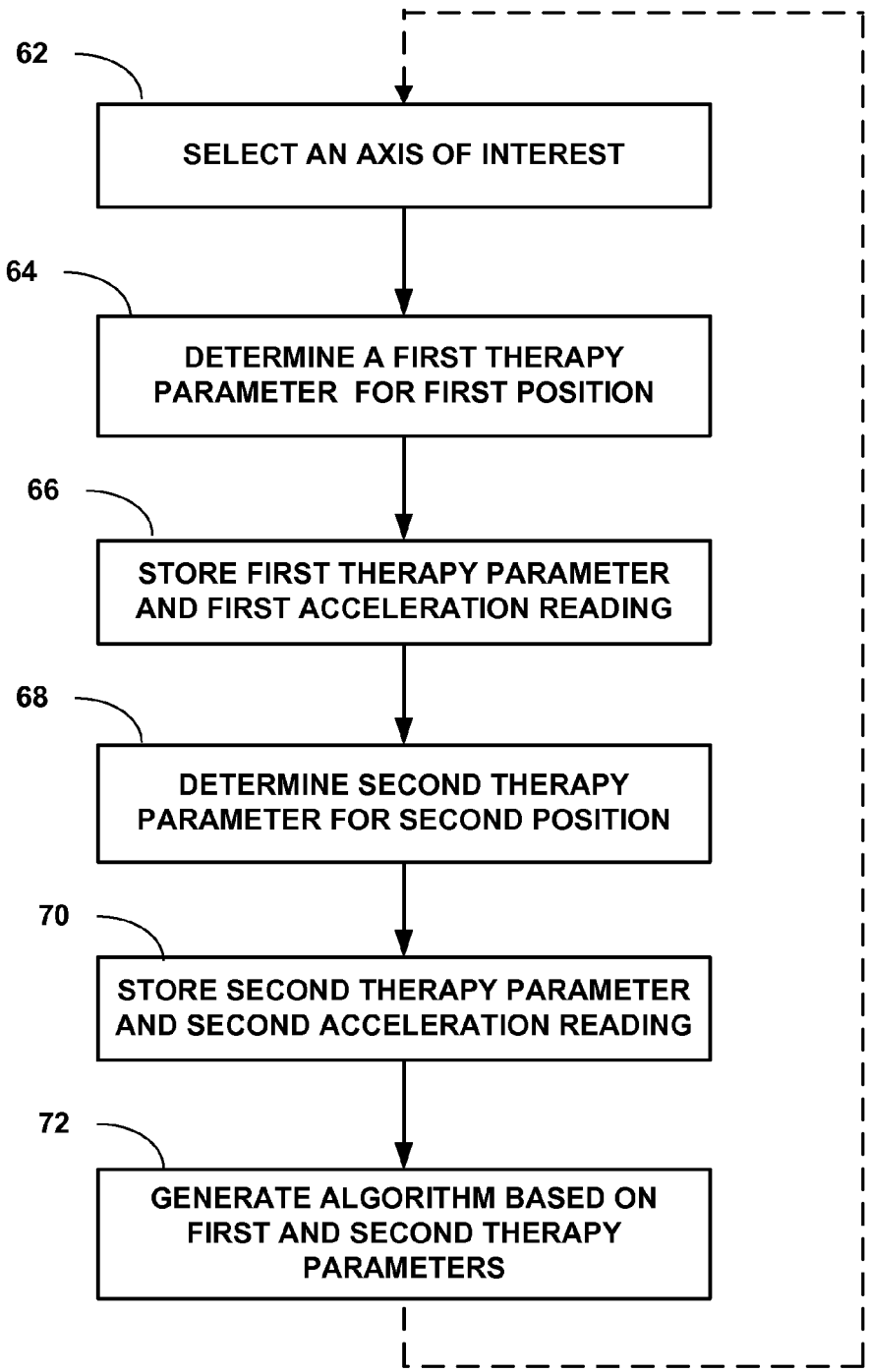
FIG. 5 is a flow chart illustrating an example technique that may be used to create an algorithm for determining one or more therapy parameters.

An example of a technique that may be used to create an algorithm for determining one or more therapy parameters is shown in the flowchart of FIG. 5. In some examples, Processor 34 may orient an acceleration vector by determining the angle between the y axis of IMD 12 and the R-C axis of the patient, as shown in FIG. 3. This may be done, for example, by determining the difference between the acceleration reading in the y axis and 1G while the patient is standing upright. Similarly, the difference between the x axis and the L-M axis and the z axis and the A-P axis may each be determined based on the difference in the acceleration reading on the x axis and 0 G while the patient is standing upright. These calculations may be done by processor 34 of IMD 12, or by a processor within programming device 20. In some examples, processor 34 may orient one axis at a time. However, as discussed below, calibration and determination of the algorithm may occur without orientation.

A physician or other clinician selects an axis of interest (62) during calibration. The axis of interest may be selected based on the orientation of sensor 40 within patient 14. In some examples, the orientation of sensor 40 may be determined based on patient feedback. For example, when sensor 40 is a single axis accelerometer, the direction of sensor 40 may be selected in order to capture the axis along which the most movement of a particular patient's spinal cord occurs. In some examples, the direction of the axis of the single axis accelerometer may be selected based on the effect of spinal cord movement in directions other than the direction selected on therapy parameter values. For example, the axis of interest may be selected based on corresponding to the largest change in therapy parameter values as acceleration values change along the axis.

After the axis of interest has been selected, a physician or other clinician may instruct the patient to assume a particular posture associated. The position may be selected in order for calibration of IMD 12 to include opposite positions along the axis of interest. For example, patient 14 may be instructed to lie on his or her back, i.e., in the supine position. While the patient is in the supine position, the clinician may adjust therapy delivered to the patient via therapy module 32 and electrodes 30 and 31 to determine a first therapy parameter or program for the first acceleration reading (64) resulting from the assumed posture. In some examples, the patient may provide feedback concerning efficiency (e.g., pain relief or relief of other symptoms) and/or side effects to the clinician to aid in determining the first therapy parameter or program. The first therapy parameter and the first acceleration are then stored in memory 36 (66). The first therapy parameter is stored along with the acceleration vector that was detected by sensor 40.

The clinician then asks the patient to assume a second position, different, and opposite, from the first position. In some examples, the patient may be asked to lie in a prone position. The change in position results in a change in acceleration registered by sensor 40 of IMD 12. While the patient is in the prone position the clinician may adjust therapy delivered to the patient via therapy module 32 and electrodes 30 and 31 to determine a second therapy parameter or program for the second position (68). Although the positions assumed by the patient may be opposite, the acceleration vectors resulting from the positions are not necessarily 180 apart. In some examples, the patient may provide feedback to the clinician to aid in determining the second therapy program associated with the second acceleration reading. Processor 34 may then store the second therapy parameter and the second acceleration reading (70). The second therapy parameter is stored along with the acceleration vector detected by sensor 40 that resulted in the second therapy parameter.

Processor 34 may then generate an algorithm based on the first and second therapy parameters or programs. For example, the therapy parameters associated with the first and second accelerations may be used to create a linear algorithm that defines a curve along which therapy parameters may be determined based on a current sensed acceleration vector. In some examples, a parabola or other non-linear equation may be used. In some examples, additional calibration readings may be collected in order to calculate additional coefficients of the non-linear equation to provide an appropriate fit for the equation to the patient. In some examples, an equation for determining the amplitude of the pulse voltage or current amplitude to be used in delivering therapy in response to a given acceleration sensed by sensor 40 may be defined by an algorithm. For voltage, as one example, the algorithm may be defined as:

$$\text{Amp}(t) = \frac{\text{Amp}(V_1) + \text{Amp}(V_2)}{|V_1 - V_2|} + \text{Amp}(V_1) * |V_p|.$$

In the above equation, Amp(t) is the voltage amplitude of the new therapy parameter to use in delivering therapy to the patient based on the patient's current posture as represented by current acceleration vector $V_t$. Amp ($V_1$) is the voltage amplitude from the first therapy parameter associated with the first acceleration vector $V_1$, e.g., the acceleration vector obtained when the patient occupied the supine position. Amp ($V_2$) is the voltage amplitude from the second therapy program associated with the second acceleration vector $V_2$, e.g., the acceleration vector obtained when the patient occupied the prone position. |Vp| is the projection of a current acceleration vector $V_t$ onto the axis of interest (which in this case is the A-P axis) as detected by sensor 40, where sensor 40 is aligned with this axis of interest. Further, $|V_1-V_2|$ is the distance between $V_1=(x_1, y_1, z1)$ and $V_2=(x_2, y_2, z_2)$ which is determined as $\sqrt{(x_1-x_2)^2+(y_1-y_2)^2+(z_1-z_2)^2}$.

In some examples, Vp is the projection of the current acceleration vector $V_t$ onto the axis of interest, which is aligned with the axis of a single axis accelerometer. In particular, $V_t$ may be projected with respect to either $V_1$ or $V_2$, either of which substantially align with the axis of interest (and the sensor axis) in one example. In some examples, the acceleration vector Vp may be a single axis vector (e.g., expressed in terms of a single axis x, y or z). The first and second acceleration vectors $V_1$ and $V_2$ serve as reference vectors for adjustment of therapy settings. The presently sensed acceleration vector $V_t$ is a vector that may be different from the first and second acceleration vectors $V_1$ and $V_2$. |Vp| may equal the equation: $|Vp|=|Vt|*\cos \Theta$, where $\Theta$ is the angle between the presently sensed acceleration vector $V_t$ and the axis of the sensor 40 as measured with respect to either $V_1$ or $V_2$, wherein $|V_t|=\sqrt{x_t^2+y_t^2+z_t^2}$. If the projection of $V_t$ onto the axis of interest is with respect to vector $V_1$ such that $\Theta$ is the angle between $V_1$ and $V_t$, then $$Amp(t) = \frac{Amp(V_1) + Amp(V_2)}{|V_1 - V_2|} + Amp(V_1)*|V_p|.$$

However, if the projection is with respect to $V_2$ such that $\Theta$ is the angle between $V_2$ and $V_t$, then $$Amp(t) = \frac{Amp(V_1) + Amp(V_2)}{|V_1 - V_2|} + Amp(V2)*|V_p|.$$

Figure 8A:
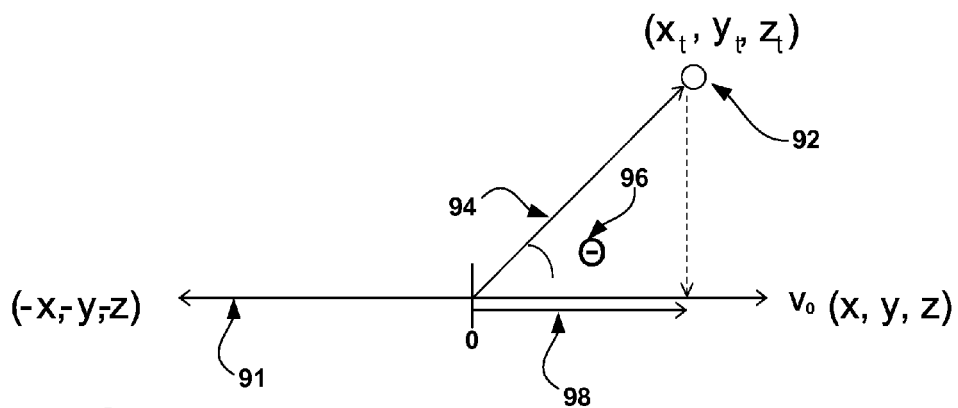
FIGS. 8A and 8B are graphs illustrating the projection of an acceleration vector onto a single axis.
Figure 8B:
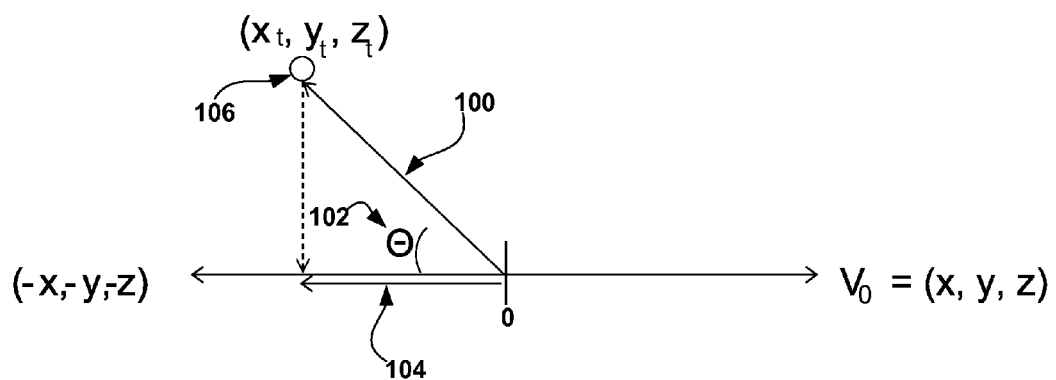

If the presently sensed acceleration vector $V_t$ is projected onto the axis of sensor 40 with respect to $V_1$, $\Theta$ may be the angle between the presently sensed acceleration vector $V_t$ and vector $V_1$. In this case, $\Theta$ may be determined by the equation $$\Theta = \cos^{-1}\left(\frac{x_t*x_1 + y_t*y_1 + z_t*z_1}{|V_t|*|V_1|}\right),$$

wherein $|V_t|=\sqrt{x_t^2+y_t^2+z_t^2}$ and $|V_1|=\sqrt{x_1^2+y_1^2+z_1^2}$. If the presently sensed acceleration vector $V_t$ is instead projected onto the axis of sensor 40 with respect to $V_2$, $\Theta$ may be the angle between the current acceleration vector $V_t$ and vector $V_2$. In this case, $\Theta$ may be determined by the equation $$\Theta = \cos^{-1}\left(\frac{x_t*x_2 + y_t*y_2 + z_t*z_2}{|V_t|*|V_2|}\right),$$

wherein $|V_t|=\sqrt{x_t^2+y_t^2+z_t^2}$ and $|V_2|=\sqrt{x_2^2+y_2^2+z_2^2}$. The magnitude and direction of projection vector Vp may be the output of an accelerometer aligned with the axis of interest (e.g., A-P axis) as projected onto the $V_1$ or $V_2$ vector in the discussed above. The projection vector Vp is illustrated in FIGS. 8A and 8B, discussed below.

In some examples, such as when the patient first lies supine and then lies prone, acceleration vector $V_1$ equals 1G in on the A-P axis and $V_2$ equals −1G on the A-P axis. In some examples, acceleration vectors $V_1$ and $V_2$ are acceleration vectors observed when a patient is in a first and a second position that are opposite of each other. In such examples, the acceleration recorded by the sensor 40 may or may not equal plus or minus 1G. The above equation provides the amplitude of voltage for movement along a single axis. In some examples, the clinician may repeat the process of selecting an axis of interest and determining therapy parameters at difference accelerations for at least one additional axis, such as the L-M axis or the R-C axis. For example, a patient may be asked to lie first on their right side and then on their left side while the IMD 12 is programmed in order to generate an algorithm for the each axis.

In some examples, the algorithm generated by processor 34 may determine the average contribution of projections onto two axes in order to provide an algorithm for determining the voltage or current amplitude for a therapy parameter where the algorithm compensates for movement of the spinal cord along two axes. An algorithm for determining the voltage amplitude, or other therapy parameter such as current amplitude, with movement along both the A-P axis and the L-M axis is as follows:

$$Amp(t) = \frac{\left(\frac{Amp(V_{ap1}) + Amp(V_{ap2})}{|V_{ap1} - V_{ap2}|} + Amp(V_{ap1})*|V_{p,ap}|\right) + \left(\frac{Amp(V_{ml1}) + Amp(V_{ml2})}{|V_{ml1} - V_{ml2}|} + Amp(V_{1ml})*|V_{p,ml}|\right)}{2}$$

Figure 7:
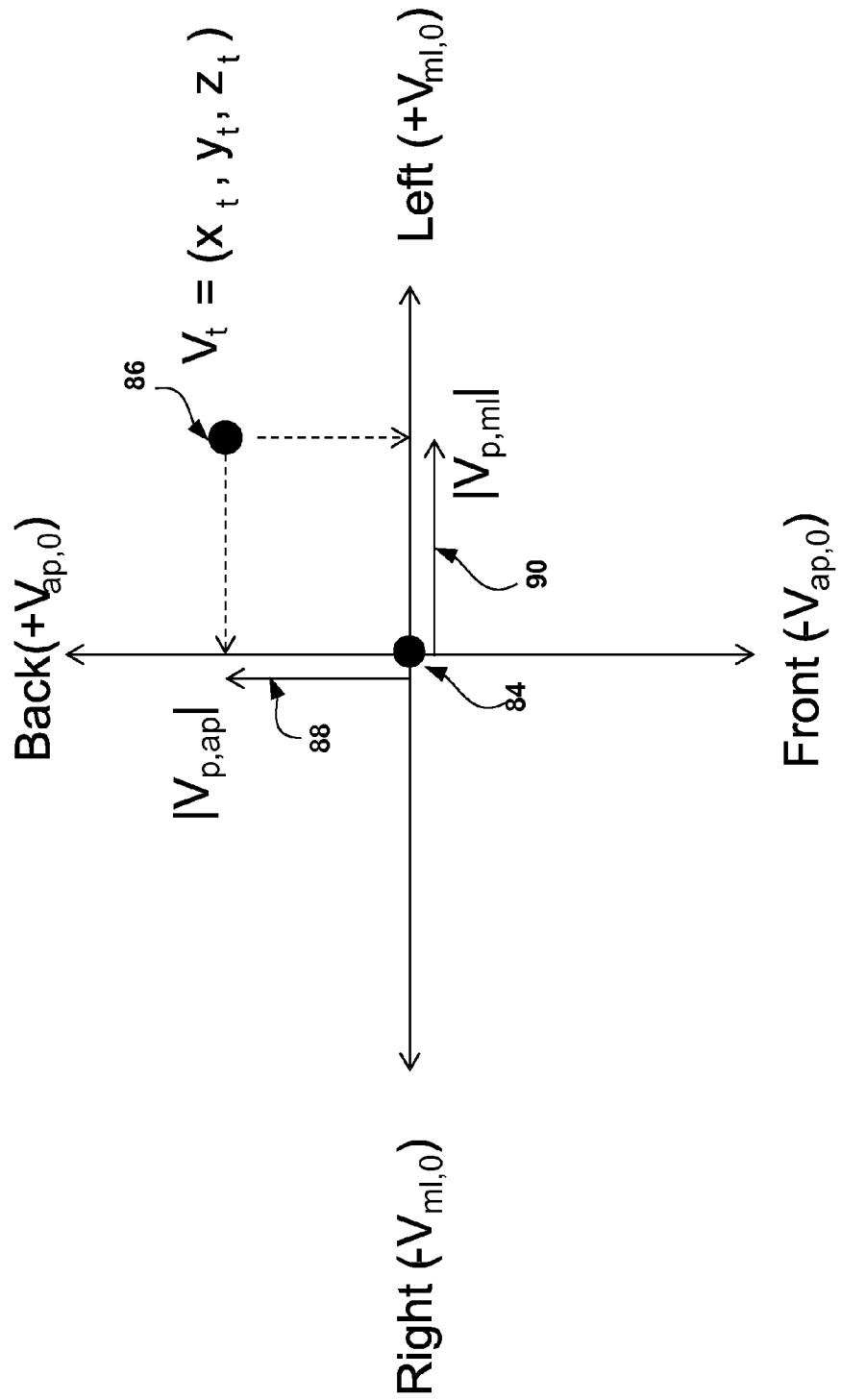
FIG. 7 is a graph illustrating spinal cord movement in two dimensions.

Amp (t) is the calculated voltage amplitude for a therapy program associated with the detected acceleration vector at the current time. Amp ($V_{ap1}$) is the voltage amplitude associated with a therapy parameter determined during calibration while a patient lies on their back (or front) and Amp ($V_{ap2}$) is the voltage amplitude associated with the patient lying in the opposite position, e.g. on their front (or back). Amp ($V_{ml1}$) is the voltage amplitude associated with a therapy parameter determined during calibration while the patient lies on their right (or left) side and Amp($V_{ml2}$) is the voltage amplitude associated with the patient lying in the opposite position, e.g., on their left (or right) side. Similarly, $V_{ap1}$ and $V_{ap2}$ are the acceleration vectors associated with the patient being in opposite positions along the A-P axis during calibration, and $V_{ml1}$ and $V_{ml2}$ are the acceleration vectors associated with the patient being in opposite positions along the L-M axis during calibration. $|V_{p,ap}|$ and $|V_{p,ml}|$ are the projections of the acceleration vector onto the A-P and L-M axes with respect to vectors $V_{ap1}$ and $V_{ml1}$, respectively, and detected by sensor 40. These respective projection values are determined in a manner similar to that described above with respect to the single axis method. In some examples, each vector projection may be used to determine a different therapy parameter. For example, $|V_{p,ap}|$ may be used to determine a current amplitude and $|V_{p,ml}|$ may be used to determine an electrode configuration. One algorithm that allows for adjustment to a therapy parameter to compensate for spinal cord movement is shown in FIG. 7 below.

In some examples, the algorithm applied by processor 34 may determine the average contribution of projections onto any number of axes in order to provide an algorithm for determining the voltage or current amplitude for a therapy where the algorithm compensates for movement of the spinal cord along the specified axes. An algorithm for determining the voltage amplitude, or other therapy parameter such as current amplitude, with movement along the specified axes is as follows:

$$\text{Amp}(t) = \frac{\sum_{1}^{NumAxes}\left(\frac{\text{Amp}(+V_{axis})+\text{Amp}(-V_{axis})}{|+V_{axis}--V_{axis}|}+\text{Amp}(+V_{axis})*|V_{p,axis}|\right)}{NumAxes}.$$

Figure 6:
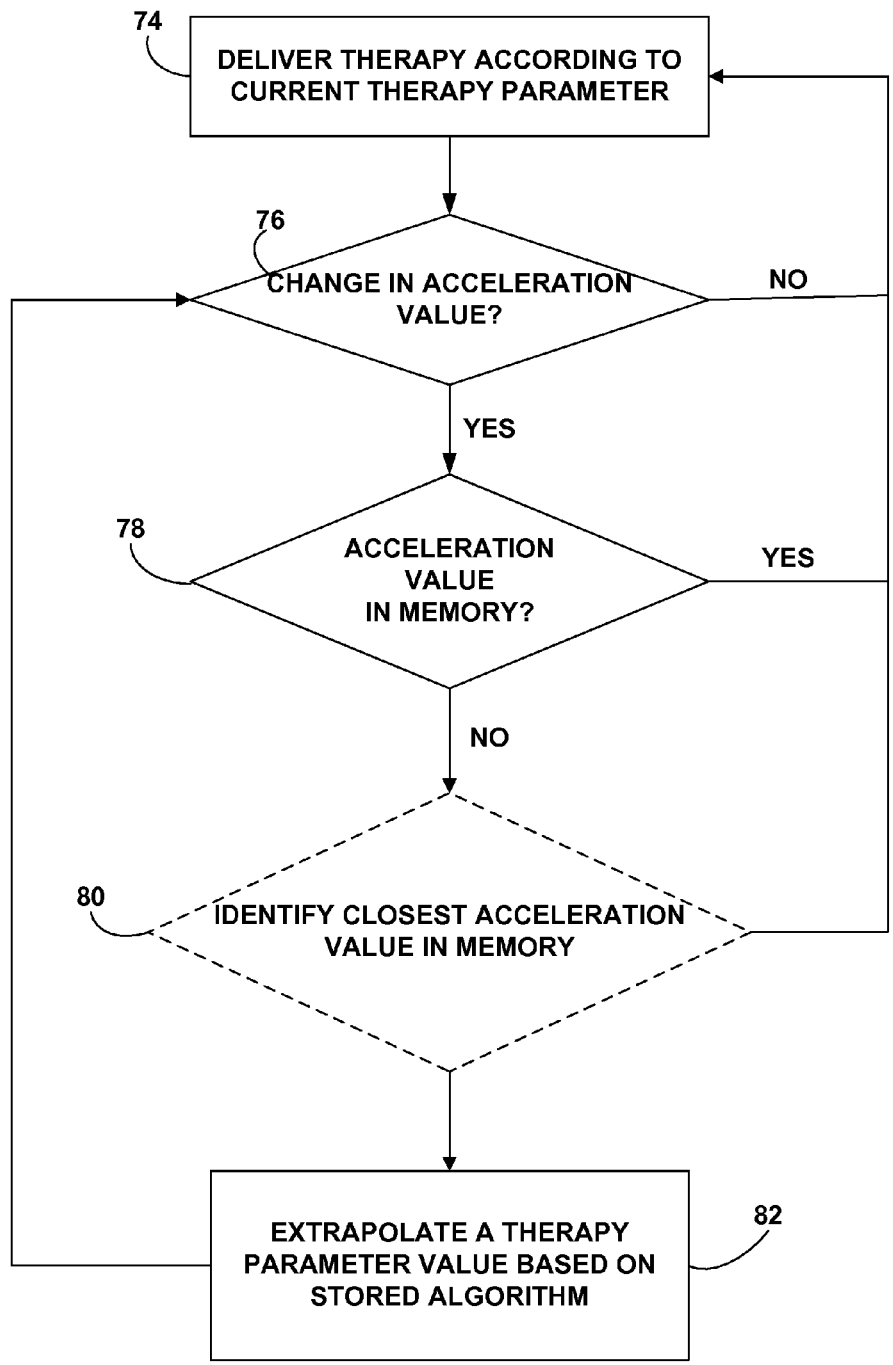
FIG. 6 is a flow chart illustrating an example technique for extrapolation of a therapy program based on two known therapy programs.

As with the algorithms for a single axis or for two axes, the above equation includes the amplitudes of a therapy parameter determined while the patient is in opposite positions along the axis, $+V_{axis}$ and $-V_{axis}$ and the acceleration values associated with each of the positions. An example of a technique that processor 34 may employ to extrapolate a therapy program based on two known therapy programs is shown in the flowchart of FIG. 6. Processor 34 may control therapy module 32 (FIG. 2) to deliver therapy according to a current therapy parameter or therapy program (74). In some examples, the therapy parameter may be stored in a table in memory 36 along with an associated acceleration value. Processor 34 monitors the output of sensor 40 to determine whether there has been a change in acceleration value (76). If there is no change in the acceleration value, control therapy module 32 continues to provide therapy to patient 14 following the previous therapy parameter or therapy program. If there has been a change in acceleration value, processor 34 accesses memory 36 to determine what acceleration values have been stored along with associated therapy parameters or programs. Processor 34 determines if the acceleration value is stored in memory 36 (78). If the acceleration value has previously been stored in memory 36 and has a therapy parameter associated with the acceleration value, then processor 34 controls therapy module 32 to delivery therapy based on the stored therapy parameter (74). If the acceleration value is not in memory 36, then processor 34 may identify the closest acceleration value in memory 36 (80). If the closest acceleration value stored in memory 36 is within a predetermined range of the sensed acceleration value, then processor 34 controls therapy module 32 to deliver therapy based on the therapy parameter associated with the stored acceleration value.

If the closest acceleration value stored in memory 36 is outside of the predetermined range, or if the closes acceleration value is not determined, then processor 34 may extrapolate a therapy parameter value based on a stored algorithm (82). In some examples, algorithm used to interpolate or extrapolate a new therapy parameter may be defined by two stored acceleration and therapy values. In some examples, the acceleration value and therapy parameter values may be associated with opposite position. In some examples, the algorithm may be a linear equation. The use of the equation may allow for the extrapolation of therapy parameter values for acceleration values outside of the acceleration values previously stored or measured. For example, the equation may allow for the determination of a therapy parameter for an acceleration value above 1 G or below -1G, where 1G may correspond to a first of the opposing patient positions and -1G may correspond to a second of the opposing patient positions. For example, the single axis linear equation discussed above may be used to determine an appropriate therapy parameter for when a force greater than 1G is felt along a patient's A-P axis. This may occur, for example, while the patient is in a car or airplane. The algorithm allows for the entry of acceleration vectors of any value. Unlike systems that determine therapy parameters based on position, this allows for adjustments for acceleration values that would not be mapped to a patient position.

FIG. 7 is a graph illustrating spinal cord movement in two dimensions. In some examples, such as the one illustrated in FIG. 7, the majority of spinal cord movement occurs in a plane that is perpendicular to the spinal column. The graph of FIG. 7 may be helpful in understanding the algorithm used to determine therapy parameters when sensor 40 is either a dual-axis accelerometer or two single axis accelerometers. Point 84 represents the location of a patient's spinal cord under zero acceleration along the A-P axis and zero acceleration along the L-M axis. In some examples, this occurs when a patient is sitting or standing upright. Point 84 is also the origin of the graph illustrating the spinal cord movement in two dimensions. Point 86 represents the current location of the spinal cord with the plane defined by the L-M and A-P axes relative to spinal cord's original position. Point 86 corresponds to an acceleration vector V at a time t, wherein $V_t=(x_t, y_t, z_t)$. Projection 88 is a projection of acceleration vector $V_t$ and point 86 onto the A-P axis. Projection 88 may be the acceleration detected by sensor 40 along the A-P axis. $|V_{p,ap}|$ is the magnitude of projection 88. Projection 90 is a projection of acceleration vector $V_t$ and point 86 onto the L-M axis. $|V_{p,ml}|$ is the magnitude of the projection 90. Projection 90 may be the acceleration detected by sensor 40 along the L-M axis. That is, projections 88 and 90 may represent the output of a dual axis accelerometer or two single axis accelerometers. Projections 88 and 90 may be used in determining an amplitude for therapy, such as a voltage or current amplitude. In some examples, the amplitude may be determined by processor 34 based on the algorithm (discussed above):

$$\text{Amp}(t) = \frac{\left(\frac{\text{Amp}(V_{ap1})+\text{Amp}(V_{ap2})}{|V_{ap1}-V_{ap2}|}+\text{Amp}(V_{ap1})*|V_{p,ap}|\right)+\left(\frac{\text{Amp}(V_{ml1})+\text{Amp}(V_{ml2})}{|V_{ml1}-V_{ml2}|}+\text{Amp}(V_{1ml})*|V_{p,ml}|\right)}{2}.$$

FIGS. 8A and 8B illustrate the projection of an acceleration vector on to a single axis. FIGS. 8A and 8B help to illustrate the single axis algorithms discussed above. In FIG. 8A point 92 represents the location of an acceleration vector relative to a predefined axis 91. In some examples the axis may be defined by a single axis accelerometer. An acceleration vector 94 is at an angle Θ 96 with the axis 91. Angle 96 can be determined using the equation $$\Theta = \cos^{-1}\left(\frac{x_t*x_0+y_t*y_0+z_t*z_o}{|V_t|*|V_0|}\right),$$

where vector $V_0$ is an acceleration vector along the axis of the single axis accelerometer. In some examples, $V_0$ may be the acceleration detected when a patient assumes one of two opposite positions. The values of $x_t, y_t, z_t$ define acceleration vector $V_t$, and $|V_t|$ is the magnitude of the acceleration vector, and $|V_0|$ is the magnitude of the acceleration vector. The magnitude of projection vector 98 is $|Vp|=|Vt|*\cos\Theta$. Projection vector 98 may be used to determine the amplitude of therapy, such as a voltage or current amplitude, being delivered to the patient. In some examples, the amplitude of projection vector 98 equals the output of sensor 40.

FIG. 8B is illustrates an acceleration projection vector 104 with a negative acceleration value. Acceleration projection vector 104 may result from a patient leaning in a direction opposite of the direction resulting in projection vector 98 in FIG. 8A. Point 106 represents the location of a patient's spinal cord that is subject to acceleration. Point 106 defines acceleration vector 100. Acceleration vector 100 is at an angle Θ 102. As discussed above with respect to FIG. 8A, the equations that explain the conversion of acceleration vector 100 to a projection onto a single axis are $$\Theta = \cos^{-1}\left(\frac{x_t * x_0 + y_t * y_0 + z_t * z_o}{|V_t| * |V_0|}\right)$$

and |Vp|=|Vt|*cos Θ. As is evidenced by the equations, if, as is the case when $V_0$ aligns with the axis onto which the vector is being projected, the values of the acceleration for two directions do have limited effect on the final projection. In fact, multiple three dimensional acceleration vectors may result in the same acceleration projection vector 104. In some examples, the orientation of a single axis accelerometer may take into consideration the fact that changes in acceleration along the other axes fail to show up in the projection vector, and therefore fail to affect any change in therapy parameter that is made based on the acceleration reading. For example, for a particular patient, a clinician or physician may choose the orientation of a single axis accelerometer based on patient feedback. This allows for the delivery of efficacious treatment with minimal computing power used.

In some examples, a patient may be asked to move into a variety of positions and provide feedback regarding the appropriate stimulation settings for those positions. The feedback may then be used to determine which axis it is most appropriate to align the accelerometer with. For example, movement along the L-M axis or the R-C axis may have minimal effect on the appropriate therapy parameters while movement along the A-P axis has a greater effect on the efficacious therapy parameters for a first patient, while for a second patient movement along the L-M axis may have a large effect on efficacious therapy parameters while movement along the A-P axis and the R-C axis is minimal. The orientation of a single axis accelerometer may, therefore, be determined on a patient specific basis.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples have been described. These and other examples are within the scope of the following claims.

The invention claimed is:

1. A method comprising:

receiving, by a processor, data representative of a first therapy parameter value for delivery of a therapy while a patient is in a first position, the first therapy parameter value associated with a first acceleration value, and a second therapy parameter value for delivery of the therapy while the patient is in a second position, the second therapy parameter value associated with a second acceleration value, wherein the first position is opposite the second position;

sensing, by an acceleration sensor, a third acceleration value;

generating, by the processor, a third therapy parameter value for delivery of a therapy to a patient based on an algorithm defined as a function of the first therapy parameter value and the second therapy parameter value, and a relationship of the third acceleration value to the first and second acceleration values; and controlling, by a therapy delivery device, a medical device to deliver the therapy to the patient based on the third therapy parameter value.

2. The method of claim 1, further comprising:

sensing the first acceleration value from the acceleration sensor while the patient is in the first position;

receiving a first therapy parameter value for delivery of the therapy to the patient while the patient is in the first position;

associating the first therapy parameter value with the first acceleration value;

sensing the second acceleration value from the acceleration sensor while the patient is in the second position;

receiving the second therapy parameter value for delivery of the therapy to the patient while the patient is in the second position; and associating the second therapy parameter value with the second acceleration value.

3. The method of claim 2, wherein the first therapy parameter value and the second therapy parameter value are generated based on patient feedback.

4. The method of claim 2, wherein the acceleration sensor is a single-axis accelerometer, the first acceleration vector value is 1G, and the second acceleration vector value is −1G.

5. The method of claim 4, wherein the third acceleration value is greater than 1G.

6. The method of claim 4, wherein the third acceleration value is between 1G and −1G.

7. The method of claim 2, further comprising selecting a first direction of the acceleration sensor for determination of the first and second acceleration values.

8. The method of claim 7, wherein the selection is based on an effect of spinal cord movement in a second direction and a third direction on the third therapy parameter value, the second and third directions being perpendicular to the first direction.

9. The method of claim 8, wherein the acceleration sensor is a single axis accelerometer, and wherein the axis of the single axis accelerometer aligns with the first direction.

10. The method of claim 8, wherein the acceleration sensor is a single axis accelerometer, and wherein the axis of the single axis accelerometer does not align with the first direction, the second direction, or the third direction.

11. The method of claim 1, wherein the third therapy parameter value is a stimulation amplitude value generated based on the formula $$\text{Amp}(t) = \frac{\text{Amp}(V_1) + \text{Amp}(V_2)}{|V_1 - V_2|} + \text{Amp}(V_1) * |V_p|,$$

wherein Amp(t) is the third therapy parameter value, Amp $(V_1)$ and Amp$(V_2)$ are the first and second therapy parameter values, respectively, $V_1$ and $V_2$ are the first and second acceleration values, respectively, and $V_p$ is the third acceleration value.

12. The method of claim 1, wherein the first position is a prone position and the second position is a supine position.

13. The method of claim 1, wherein the first position and the second position are at least one of the following opposing patient position pairs:
   supine and prone,
   left side and right side, and
   upright and upside down.

14. The method of claim 13, wherein the opposing patient position pair is selected based on an axis of interest.

15. The method of claim 1, wherein the therapy is electrical stimulation therapy.

16. A medical device system comprising:
   an acceleration sensor configured to detect a first acceleration value while a patient is in a first position, a second acceleration value while the patient is in a second position, and a third acceleration value while the patient is in a third position, the first position opposite the second position;
   a processor configured to:
      receive data representative of a first therapy parameter value for delivery of a therapy while the patient is in the first position, the first therapy parameter value associated with the first acceleration value, and a second therapy parameter value for delivery of therapy while the patient is in the second position, the second therapy parameter value associated with the second acceleration value, and
      generate a third therapy parameter value for delivery of a therapy to the patient based on an algorithm defined as a function of the first therapy parameter value and the second therapy parameter value, and a relationship of the third acceleration value to the first and second acceleration values; and
   a therapy delivery module configured to deliver the therapy to the patient based on the third parameter value.

17. The system of claim 16, wherein the processor is further configured to: receive the first therapy parameter value while the patient is in the first position;
   associate the first therapy parameter value with the first acceleration value;
   receive the second therapy parameter value while the patient is in the second position; and
   associate the second therapy parameter value with the second acceleration value.

18. The system of claim 16, wherein the third therapy parameter value is generated based on the formula $$\text{Amp}(t) = \frac{\text{Amp}(V_1) + \text{Amp}(V_2)}{|V_1 - V_2|} + \text{Amp}(V_1) * |V_p|,$$

wherein Amp(t) is the third therapy parameter value, Amp $(V_1)$ and Amp$(V_2)$ are the first and second therapy parameter values, respectively, $V_1$ and $V_2$ are the first and second acceleration values, respectively, and $V_p$ is the third acceleration value.

19. The system of claim 18, further comprising a programmer configured to receive patient feedback and wherein the first therapy parameter value and the second therapy parameter value are generated based on patient feedback.

20. The system of claim 19, wherein the acceleration sensor is a single axis accelerometer, the first acceleration vector value is 1G, and the second acceleration vector value is −1G.

21. The system of claim 19, wherein the third acceleration value is between 1G and −1G.

22. The system of claim 19, wherein the third acceleration value is greater than 1G.

23. The system of claim 18, wherein the third therapy parameter value is an electrical current amplitude.

24. The system of claim 16, wherein the first position is a prone position and the second position is a supine position.

25. The system of claim 16, wherein the processor is further configured to select a first direction of the acceleration sensor for determination of the first and second acceleration values.

26. The system of claim 25, wherein the selection is based on an effect of spinal cord movement in a second and third direction on the third therapy parameter value, the second and third directions perpendicular to the first direction.

27. The system of claim 26, wherein the acceleration sensor is a single axis accelerometer, and wherein the axis of the single axis accelerometer aligns with the first direction.

28. The system of claim 26, wherein the acceleration sensor is a single axis accelerometer and wherein the axis of the single axis accelerometer does not align with the first direction, the second direction, or the third direction.

29. The system of claim 16, wherein the first position and the second position are at least one of opposing position pairs:
   supine and prone,
   left side and right side, and
   upright and upside down.

30. The system of claim 29, wherein the processor is further configured to select the opposing patient position pair based on an axis of interest.

31. The system of claim 16, wherein the therapy delivery module is further configured to deliver electrical stimulation therapy.

32. The system of claim 16, wherein the acceleration sensor is further configured to:
   detect a fourth acceleration value while the patient is in fourth position, and a fifth acceleration value while the patient is in a fifth position, the fourth position opposite the fifth position, and the first and second positions different than the fourth and fifth positions, and
   the processor is further configured to:
   receive data representative of a fourth therapy parameter value for delivery of the therapy while the patient is in the fourth position, the fourth therapy parameter value associated with the fourth acceleration value, and a fifth therapy parameter value for delivery of the therapy while the patient is in the fifth position, the fifth therapy parameter value associated with the fifth acceleration value, and
   generate the third therapy parameter value for delivery of the therapy to the patient based on the first therapy parameter value, the second therapy parameter value, the fourth therapy parameter value, the fifth therapy parameter value, the relationship of the third acceleration value to the first and second acceleration values, and a relationship of the third acceleration value to the fourth and fifth acceleration values.

33. The system of claim 32, wherein the third therapy parameter value is generated based on the formula $$Amp(t) = \frac{\left(\frac{Amp(V_{ap1}) + Amp(V_{ap2})}{|V_{ap1} - V_{ap2}|} + Amp(V_{ap1}) * |V_{p,ap}|\right) + \left(\frac{Amp(V_{ml1}) + Amp(V_{ml2})}{|V_{ml1} - V_{ml2}|} + Amp(V_{1ml}) * |V_{p,ml}|\right)}{2},$$

wherein Amp(t) is the third therapy parameter value, Amp ($V_{ap1}$) and Amp ($V_{ap2}$) are the first and second therapy parameters values, respectively, Amp ($V_{ml1}$) and Amp ($V_{ml2}$) are the fourth and fifth therapy parameter values, respectively, $V_{ap1}$, $V_{ap2}$, $V_{ml1}$, and $V_{ml2}$ are the first, second, fourth and fifth acceleration values, respectively, $|V_{p,ap}|$ is a projection of the third acceleration value with respect to $V_{ap1}$, and $|V_{p,ml1}|$ is a projection of the third acceleration value with respect to $V_{ml1}$.

34. A non-transitory computer-readable medium comprising instructions for causing a programmable processor to:
receive, by the processor, data representative of a first therapy parameter value for delivery of a therapy while a patient is in a first position, the first therapy parameter value associated with a first acceleration value generated by an acceleration sensor, and a second therapy parameter value for delivery of the therapy while the patient is in a second position, the second therapy parameter value associated with a second acceleration value generated by the acceleration sensor, wherein the first position is opposite the second position;
receive, by the processor, a third acceleration value;
generate, by the processor, a third therapy parameter value for delivery of the therapy to the patient based on an algorithm defined as a function of the first therapy parameter value and the second therapy parameter value, and a relationship of the third acceleration value to the first and second acceleration values; and
control a therapy delivery module of a medical device to deliver the therapy to the patient based on the third therapy parameter value.

35. A system comprising:
means for receiving, by a processor, data representative of a first therapy parameter value for delivery of a therapy while a patient is in a first position, the first therapy parameter value associated with a first acceleration value generated by an acceleration sensor, and a second therapy parameter value for delivery of the therapy while the patient is in a second position, the second therapy parameter value associated with a second acceleration value generated by the acceleration sensor, wherein the first position is opposite the second position;
means for sensing, by the processor, a third acceleration value;
means for generating, by the processor, a third therapy parameter value for delivery of a therapy to a patient based on an algorithm defined as a function of the first therapy parameter value and the second therapy parameter value, and a relationship of the third acceleration value to the first and second acceleration values; and
means for controlling a therapy delivery module of a medical device to deliver the therapy to the patient based on the third therapy parameter value.

* * * * *